(12) United States Patent
Onishi et al.

(10) Patent No.: US 7,550,596 B2
(45) Date of Patent: Jun. 23, 2009

(54) METHOD OF PRODUCING ETHYL (3R, 5S, 6E)-7-[2 CYCLOPROPYL-4-(FLUOROPHENYL) QUINOLINE-3-YL]-3, 5-DIHYDROXY-6-HEPTENOATE

(75) Inventors: Atsushi Onishi, Tsukuba (JP); Kozo Tachibana, Tsukuba (JP)

(73) Assignees: Daicel Chemical Industries, Ltd., Osaka (JP); Nissan Chemical Industries, Ltd., Tokyo (JP)

( * ) Notice: Subject to any disclaimer, the term of this patent is extended or adjusted under 35 U.S.C. 154(b) by 634 days.

(21) Appl. No.: 11/254,864

(22) Filed: Oct. 21, 2005

(65) Prior Publication Data

US 2006/0089381 A1 Apr. 27, 2006

Related U.S. Application Data

(63) Continuation of application No. PCT/JP2004/005894, filed on Apr. 23, 2004.

(30) Foreign Application Priority Data

Apr. 24, 2003 (JP) ............................. 2003-119807

(51) Int. Cl.
*C07D 215/38* (2006.01)
(52) U.S. Cl. .................................... 546/157
(58) Field of Classification Search ............. 546/157
See application file for complete search history.

(56) References Cited

U.S. PATENT DOCUMENTS

| | | | | |
|---|---|---|---|---|
| 5,011,930 | A * | 4/1991 | Fujikawa et al. | 546/101 |
| 5,939,552 | A | 8/1999 | Ikeda et al. | |
| 6,533,936 | B1 * | 3/2003 | Ikeda | 210/635 |
| 7,371,865 | B2 * | 5/2008 | Acemoglu et al. | 546/173 |

| | | | |
|---|---|---|---|
| 2003/0232989 | A1 | 12/2003 | Antons et al. |
| 2004/0060871 | A1 * | 4/2004 | Onishi et al. ............. 210/656 |
| 2005/0075502 | A1 | 4/2005 | Onishi et al. |

FOREIGN PATENT DOCUMENTS

| | | |
|---|---|---|
| EP | 1 334 967 A1 | 8/2003 |
| EP | 1 354 865 A1 | 10/2003 |
| WO | WO-95/23125 A1 | 8/1995 |
| WO | WO-02/30903 A1 | 4/2002 |
| WO | WO-2004/026838 A1 | 4/2004 |

OTHER PUBLICATIONS

Shigeo Makino, "Separation of chiral compounds", Pharm Tech Japan, 1996, vol. 12, No. 1, pp. 43-52 with a partial English translation.

Shigeo Makino et al., Bunri Gijutsu, 1996, vol. 26, No. 6, pp. 15-19 with a partial English translation.

Yoshio Okamoto et al., "Polysaccharide Derivatives for Chromatographic Separation of Enantiomers", Angew. Chem. Int. Ed., 1998, vol. 37, pp. 1020-1043.

Eiji Yashima et al., "Polysaccharide-Based Chiral LC Columns", SYNLETT, 1998, pp. 344-360.

S. Nagamatsu et al., "Chiral separation of a pharmaceutical intermediate by a simulated moving bed process", Journal of Chromatography A, 1999, 832, pp. 55-65.

* cited by examiner

*Primary Examiner*—D. Margaret Seaman
(74) *Attorney, Agent, or Firm*—Birch, Stewart, Kolasch & Birch, LLP

(57) ABSTRACT

A method of producing Ethyl(3R,5S,6E)-7-[2-cyclopropyl-4-(4-fluorophenyl)quinoline-3-yl]-3,5-dihydroxy-6-heptenoate by means of liquid chromatography using a packing material comprising a carrier and, carried thereon, a polysaccharide derivative, wherein a part or all of the hydrogen atoms of hydroxyl and amino groups of the polysaccharide derivative are substituted with one or more substituents, such as a carbamoyl group wherein one hydrogen atom is substituted with an aromatic group having a specific alkyl group. The method allows the production of the above (3R,5S,6E) isomer with enhanced productivity to a conventional method.

9 Claims, 2 Drawing Sheets

METHOD OF PRODUCING ETHYL (3R, 5S, 6E)-7-[2 CYCLOPROPYL-4-(FLUOROPHENYL) QUINOLINE-3-YL]-3, 5-DIHYDROXY-6-HEPTENOATE

This application is a continuation of international application PCT/JP2004/005894, which was filed Apr. 24, 2004 and which designated the United States. The entire disclosure of PCT/JP2004/005894 is hereby expressly incorporated by reference. Applicants claim the benefit under 35 U.S.C. §120 of the filing date of PCT/JP2004/005894. Applicants also claim the benefit, under 35 U.S.C. §119, of the filing date of JP2003-119807, filed Apr. 24, 2003. The entire disclosure of JP 2003-119807 is hereby expressly incorporated by reference.

TECHNICAL FIELD

The present invention relates to a method of producing a statin-based compound useful in preventing and curing hyperlipidemia, arteriosclerosis, and the like. More particularly, the present invention relates to a method of producing optically active Ethyl (3R,5S,6E)-7-[2-cyclopropyl-4-(4-fluorophenyl)quinoline-3-yl]-3,5-dihydroxy-6-heptenoate.

BACKGROUND ART

In general, optical isomers, which are isomers having relation of a mirror image and a real image, are identical in physical and chemical properties except a rotatory power. Therefore, it is difficult to obtain only one isomer at high optical purity.

Accordingly, a cheap racemic body which is an equivalent mixture of optical isomers is typically used for a material or the like where emphasis is placed on chemical and physical properties. Meanwhile, an optically active substance composed only of one isomer has been used in many cases in the fields of drugs, biochemistry-related industry, and the like. This is because of one of the important properties of an optical isomer: the optical isomers may show different interactions when they affect an optically active substance.

For this reason, in the real state, in particular in case of drugs, the development of a drug composed of a single optically active substance intended for reducing a dosage for preventing damage from medicines and for suppressing side effects has been desired in consideration of the possibility that optical isomers may show different drug effects, different side effects, and the like between each of the optical isomers to living body (which is an optically active substance composed of an optically active amino acid, an optically active sugar, and the like).

As described above, to obtain an optically active substance having high optical purity is more difficult and more expensive than the production of a racemic body. Various methods have been attempted to solve the problem.

The methods are roughly classified into: a method involving optically resolving a racemic body to obtain one optically active substance; a method involving directly producing an optically active substance from a prochiral compound; and a method called a chiral pool method involving producing a target optically active substance by means of a cheap optically active substance as a starting material. Each method has its merits and demerits, and, at present, it has been difficult to satisfy all the items concerning productivity by means of a single method.

Examples of the method involving optically resolving a racemic body to obtain one optically active substance include crystallization by means of a diastereomer salt, a bio method such as asymmetric utilization, and a method of producing an optically active substance according to liquid chromatography.

A method of producing an optically active substance according to liquid chromatography recently developed has a potential to contribute to the quick establishment of a production approach including the setting of production conditions once analysis conditions are set because the method of producing an optically active substance is applicable to a wide variety of optical isomer compounds and because a large number of techniques for analyzing the optical purity of an optical isomer have involved the use of a separating column for an optical isomer at present (see, for example, Shigeo Makino, PHARM TECH JAPAN, 12, 43 (1996), Shigeo Makino, Tetsuji Yanami, Bunri Gijutsu, 26, 15 (1996), Y. Okamoto, Angew. Chem. Int. Ed., 37, 1020 (1998), and Y. Okamoto, Synlett, 1998, 344).

Several papers (see, for example, J. Chromatogr., A, 832, 55 (1999)) have been reported heretofore for a technique to producing Ethyl (3R,5S,6E)-7-[2-cyclopropyl-4-(4-fluorophenyl)quinoline-3-yl]-3,5-dihydroxy-6-heptenoate. In addition, patents have been filed heretofore for the production technique (see, for example, WO 02/30903 and WO 95/23125). However, the development a packing material for separating an optical isomer and a production approach that can show improved productivity has been strongly desired.

The present invention provides a method of producing Ethyl (3R,5S,6E)-7-[2-cyclopropyl-4-(4-fluorophenyl)quinoline-3-yl]-3,5-dihydroxy-6-heptenoate with higher productivity than that of a conventional method.

DISCLOSURE OF THE INVENTION

The inventors of the present invention have made extensive studies of the above method. As a result, they have found a packing material for separating an optical isomer showing high preparative productivity on Ethyl (3R,5S,6E)-7-[2-cyclopropyl-4-(4-fluorophenyl)quinoline-3-yl]-3,5-dihydroxy-6-heptenoate, thereby completing the present invention.

That is, the present invention is a method of producing Ethyl (3R,5S,6E)-7-[2-cyclopropyl-4-(4-fluorophenyl)quinoline-3-yl]-3,5-dihydroxy-6-heptenoate comprising separating Ethyl (3R,5S,6E)-7-[2-cyclopropyl-4-(4-fluorophenyl)quinoline-3-yl]-3,5-dihydroxy-6-heptenoate from a solution which comprises a mixture of optical isomers of Ethyl 6E-7-[2-cyclopropyl-4-(4-fluorophenyl)quinoline-3-yl]-3,5-dihydroxy-6-heptenoate (which may hereinafter be referred to as the "mixed solution") by means of liquid chromatography using a packing material comprising a carrier and a polysaccharide derivative carried on the carrier, in which the polysaccharide derivative has one or two or more kinds of substituents, each represented by the following general formula (1) or (2), substituted for part or whole of hydrogen atoms of hydroxyl and amino groups of a polysaccharide.

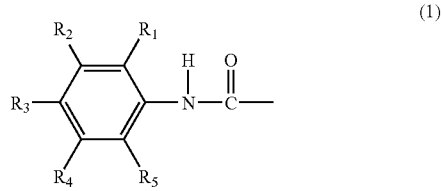
(1)

(In the formula, at least one of $R_1$ to $R_5$ represents a linear or branched alkyl group having 3 to 8 carbon atoms.)

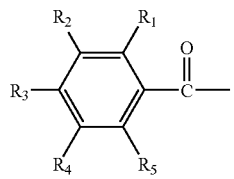

(2)

(In the formula, at least one of $R_1$ to $R_5$ represents a linear or branched alkyl group having 3 to 8 carbon atoms.)

BEST MODE FOR CARRYING OUT THE INVENTION

Figure 1:
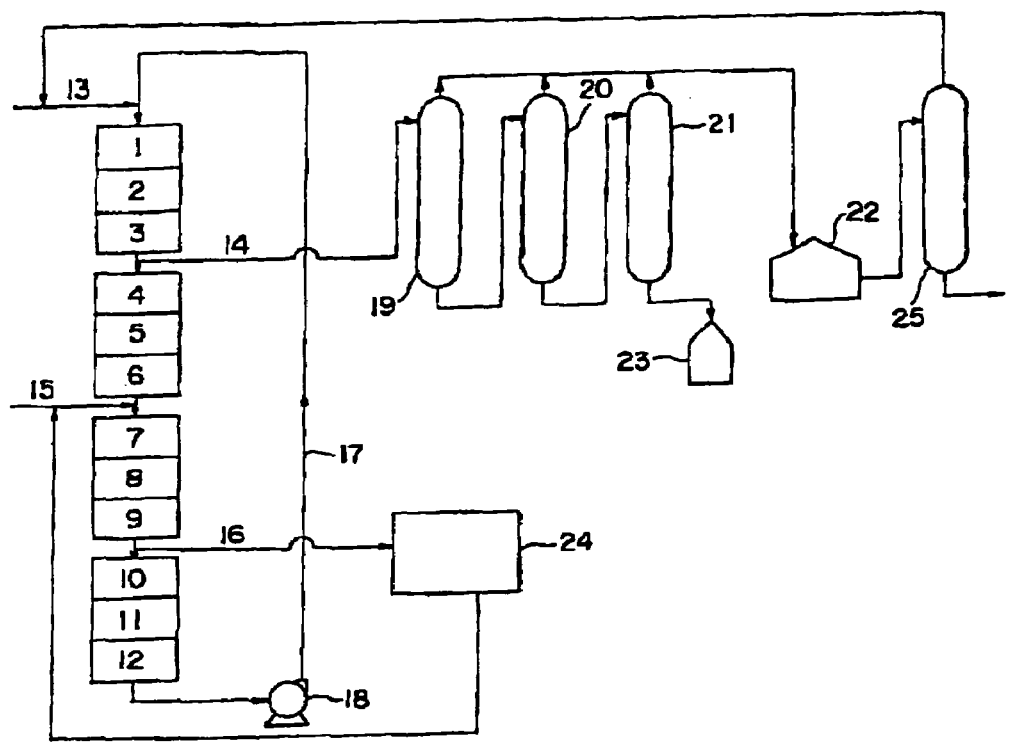
FIG. 1 is a schematic view showing an example of a simulated moving bed apparatus to be used in the present invention.

Hereinafter, an embodiment of the present invention will be described in detail.

In the present invention, Ethyl (3R,5S,6E)-7-[2-cyclopropyl-4-(4-fluorophenyl)quinoline-3-yl]-3,5-dihydroxy-6-heptenoate is separated from the mixed solution by means of liquid chromatography using a packing material to produce Ethyl (3R,5S,6E)-7-[2-cyclopropyl-4-(4-fluorophenyl)quinoline-3-yl]-3,5-dihydroxy-6-heptenoate.

The packing material to be used in the present invention comprises a carrier and a polysaccharide derivative carried on the carrier. In the polysaccharide derivative, hydrogen atoms of hydroxyl and amino groups of a polysaccharide are substituted in whole or in part by one or two or more kinds of substituents each represented by the general formula (1) or (2).

The polysaccharide may be any one of a natural polysaccharide, a natural product-denatured polysaccharide, and a synthetic polysaccharide, and is not particularly limited so long as it is optically active. Examples of the polysaccharide include α-1,4-glucan (amylose, amylopectin), β-1,4-glucan (cellulose), α-1,6-glucan (dextran), β-1,4-glucan (pustlan), α-1,3-glucan, β-1,3-glucan (curdlan, disofilan, or the like), β-1,2-glucan (Crawn Gall polysaccharide), β-1,4-galactan, α-1,6-mannan, β-1,4-mannan, β-1,2-fructan (inulin), β-2,6-fructan (levan), β-1,4-xylan, β-1,3-xylan, β-1,4-N-acetylchitosan (chitin), pullulan, agarose, alginic acid, and cyclodextrin.

Of those, cellulose, amylose, β-1,4-mannan, inulin, curdlan, and the like are preferable because these polysaccharides are readily available at high purity. In particular, cellulose and amylose are preferable. Furthermore, cellulose is desirable.

Those polysaccharides each have a number average degree of polymerization (average number of monosaccharide units such as pyranose and furanose in one molecule) of 5 or more, or preferably 10 or more. On the other hand, there is no particular upper limit on the number average degree of polymerization, but the number average degree of polymerization is preferably 1,000 or less because of the ease of handling, and is particularly preferably 500 or less.

The polysaccharide derivative may have both a substituent represented by the general formula (1) and a substituent represented by the general formula (2), or may have only one of those substituents. The distribution of the substituent in the polysaccharide derivative may be uniform or nonuniform.

The number of the substituents bound to one monosaccharide unit may be the same in all the substituents, or may be different one another. In addition, the positions of the substituents bound to each of the monosaccharide units may be the positions of specific hydroxyl and amino groups in the monosaccharide unit, or may have no particular regularity.

The polysaccharide derivative is more preferably a polysaccharide carbamate derivative having a substituent represented by the general formula (1).

In each of the general formulae, at least one of $R_1$ to $R_5$ represents a linear or branched alkyl group having 3 to 8 carbon atoms, and the others each represent a substituent selected from hydrogen, a halogen, and an alkyl group. The alkyl group is preferably a propyl group having 3 carbon atoms, and is more preferably an isopropyl group which is a branched alkyl group having 3 carbon atoms.

The substitution position of an alkyl group and the number of substituents are not particularly limited, but the alkyl group is preferably positioned at a position 4 ($R_3$). More preferably, the alkyl group is positioned at the position 4 ($R_3$) and $R_1$, $R_2$, $R_4$, and $R_5$ each represent a hydrogen atom.

A polysaccharide carbamate derivative that can be suitably adopted as a polysaccharide derivative in the present invention can be produced by means of a conventionally known method through, for example, a reaction between phenyl isocyanate having the alkyl group and a polysaccharide. A polysaccharide ester derivative can be produced by means of a conventionally known method through, for example, a reaction between an acid chloride of benzoic acid having the alkyl group and a polysaccharide.

In the present invention, the degree of introduction of the substituents in the polysaccharide derivative is usually 10% to 100%, preferably 30% to 100%, and more preferably 80% to 100%. The degree of less than 10% is not preferable because frequently little ability of optical resolution is obtained. In addition, the degree of less than 30% is not preferable because optical resolution is sometimes insufficient depending upon the kinds and concentrations of the mixed components to be optically resolved. The degree in excess of 80% is preferable because particles having excellent ability of separating an optical isomer can be obtained.

The degree of introduction of the substituents can be adjusted by, for example, an amount of the phenyl isocyanate or the acidic chloride, and can be determined by elemental analysis or NMR analysis of each change of carbon, hydrogen, and nitrogen before and after the introduction of the substituents.

A carrier to be used in the present invention is not particularly limited so long as it is a carrier that can be typically used for a packing material for liquid chromatography. Examples of such carrier include a porous organic carrier and a porous inorganic carrier.

Examples of the suitable porous organic carrier include polymers consisting of polystyrene, polyacrylamide, polyacrylate, or the like.

Examples of the suitable porous inorganic carrier include silica, alumina, magnesia, glass, kaolin, titanium oxide, silicates, and hydroxy apatite. A preferable carrier as the carrier is the porous inorganic carrier, and the particularly preferable carrier is silica gel.

The particle size of silica gel is preferably 0.1 µm to 10 mm, more preferably 1 µm to 300 µm, and even more preferably 15 to 75 µm. The average pore size of pores formed on the surface of silica gel is preferably 10 Å to 100 µm, and more preferably 50 Å to 50,000 Å.

The surface of silica gel is desirably treated to eliminate the effects of the remaining silanol. However, it will not cause any problems if the surface is not treated at all.

The carried amount of the polysaccharide derivative on the carrier is preferably 10 mass % or more with respect to the packing material, and is more preferably 15 mass % or more in terms of productivity. The carried amount is represented in a ratio of the mass of the polysaccharide derivative in the mass of the packing material. There is no particular upper limit on the carried amount, but the carried amount is not preferably 60% or more because separation efficiency reduces owing to a reduction in theoretical plate number.

The packing material can be obtained by means of any one of the conventionally known methods of producing the packing material such as a method involving chemically bonding a polysaccharide derivative directly to a carrier and a method involving applying a polysaccharide derivative to a carrier and distilling a solvent off.

At this time, the solvent to be used for dissolving the polysaccharide derivative may be any one of the organic solvents typically used so long as it is capable of dissolving the polysaccharide derivative. The organic solvent more preferably has a low boiling point or high volatility.

Furthermore, the polysaccharide derivative may be more strongly fixed on the carrier by forming additional chemical bonding through one or two or more kinds of reactions such as: chemical bonding between polysaccharide derivatives on the carrier; chemical bonding using a third component interposed between the carrier and the polysaccharide derivative; reactions on the basis of irradiation of the polysaccharide derivative on the carrier with light, radial rays such as γ rays, and electromagnetic waves such as a microwave; and a reaction based on the generation of a radical due to a radical initiator or the like.

The production method of the present invention is performed by means of liquid chromatography. The liquid chromatography may be batch-type liquid chromatography in which at least one of: the supply of a mixed solution comprising two or more kinds of components; and the discharge of an eluent (a mobile phase) is intermittently performed, but is preferably continuous liquid chromatography with which one kind of component can be continuously separated and collected from the mixed solution.

Simulated moving bed liquid chromatography which is a continuous chromatography preparation method using a general organic solvent or water as a mobile phase, supercritical chromatography using a supercritical fluid as a mobile phase, continuous simulated moving bed supercritical chromatography, or the like are particularly preferably used as such liquid chromatography.

The mixed solution contains a mixture of optical isomers of Ethyl 6E-7-[2-cyclopropyl-4-(4-fluorophenyl)quinoline-3-yl]-3,5-dihydroxy-6-heptenoate. The mixed solution may contain any other component that can be separated from the ethyl heptenoate by the polysaccharide derivative. Examples of the other component include a diastereomer of the ethyl heptenoate and a by-product in a synthesis reaction of the ethyl heptenoate.

Examples of the mixed solution include a reaction liquid obtained by the synthesis of the ethyl heptenoate, an extract liquid obtained by extracting an object from the reaction liquid, an extract liquid obtained by extracting the ethyl heptenoate from a composition containing the ethyl heptenoate, and a solution prepared by dissolving a component extracted from the extract liquid into an appropriate solvent.

Ethyl (3R,5S,6E)-7-[2-cyclopropyl-4-(4-fluorophenyl)quinoline-3-yl]-3,5-dihydroxy-6-heptenoate separated by means of the liquid chromatography is collected as a solution of Ethyl (3R,5S,6E)-7-[2-cyclopropyl-4-(4-fluorophenyl)quinoline-3-yl]-3,5-dihydroxy-6-heptenoate. Ethyl (3R,5S,6E)-7-[2-cyclopropyl-4-(4-fluorophenyl)quinoline-3-yl]-3,5-dihydroxy-6-heptenoate is obtained by concentrating the solution or by distilling the solvent of the solution off.

The simulated moving bed chromatography comprises the steps of: supplying an eluent to an endless conduit formed by connecting in series a plurality of columns in each of which the packing material is packed; discharging part of a liquid flowing through the conduit from a position on a downstream side with respect to the supplying position of the eluent in the direction in which the eluent flows in the conduit (which may hereinafter be referred to as the "first discharging step"); supplying the mixed solution to a position on a downstream side with respect to the discharging position of the liquid (which may hereinafter be referred to as the "first discharge position") in the direction in which the eluent flows in the conduit; discharging part of the liquid flowing through the conduit from a position between the supplying position of the mixed solution and the supplying position of the eluent in the conduit (which may hereinafter be referred to as the "second discharging step", and the position at which the liquid is discharged by the step may hereinafter be referred to as the "second discharge position"); moving the supplying position of the eluent, the first discharge position, the supplying position of the mixed solution, and the second discharge position to a downstream direction of the flow of the liquid while maintaining their relative positional relationship, to thereby supply the mixed solution to the position of a mixed component in the mixed solution in the conduit; and collecting a component in the liquid discharged from the conduit.

In the simulated moving bed chromatography, in the conduit, a component in the mixed solution adsorbed more readily to a packing material (which may hereinafter be referred to as the "extract component") and a component therein which is harder to be adsorbed to a packing material (which may hereinafter be referred to as the "raffinate component") are adsorbed to the packing material.

The rate at which the extract component moves in the conduit is lower than the rate at which the raffinate component moves and the rate at which the supplying position of the mixed solution moves, so the extract component is distributed on an upstream side in the supplying position of the mixed solution.

On the other hand, the rate at which the raffinate component moves in the conduit is larger than the rate at which the extract component moves and the rate at which the supplying position of the mixed solution moves, so the raffinate component is distributed on a downstream side in the supplying position of the mixed solution.

The concentration of each component supplied from the supplying position of the mixed solution increases with time until it reaches equilibrium, and the concentration distribution of the extract component is distributed on the upstream side of the supplying position of the mixed solution with its peak placed near the supplying position of the mixed solution. On the other hand, the concentration distribution of the raffinate component is distributed on the downstream side of the supplying position of the mixed solution with its peak placed near the supplying position of the mixed solution.

When both ends of the concentration distribution of each component broadening with time reach the respective discharge positions, each solution containing each component is discharged from the conduit. The concentration and distribution of each component are adjusted by various conditions such as: the size of each of the columns; the kind of the packing material; the kind of the liquid to be supplied to the conduit; the rate at which the liquid is supplied; the rate at which each liquid is discharged from the conduit; and the relative positional relationship among the supplying positions and the discharge positions and the rates at which the positions move (switching rates).

The mixed component is a component in which the extract component and the raffinate component in the mixed solution are simultaneously present. The position of the mixed component is not particularly limited so long as it is a position in the conduit in which the extract component and the raffinate component are simultaneously present. However, the position is preferably such that the extract component and the raffinate component are simultaneously present in an equivalent amount.

The relative positional relationship among the supplying position of the eluent, the first discharge position, the supplying position of the mixed solution, and the second discharge position may be such that they are positioned at substantially equal intervals in the conduit, or may be such that they are positioned at different intervals therein.

The times at which those positions are moved can be determined through, for example, analysis of a component in a liquid flowing through the conduit or simulation by means of a computer in which conditions such as the kind of the packing material and the flow rate of a liquid in the conduit are set.

The simulated moving bed liquid chromatography can be performed by means of a simulated moving bed (SMB) apparatus to be typically used disclosed in, for example, WO 95/23125 or JP-A-09-206502.

Figure 2:
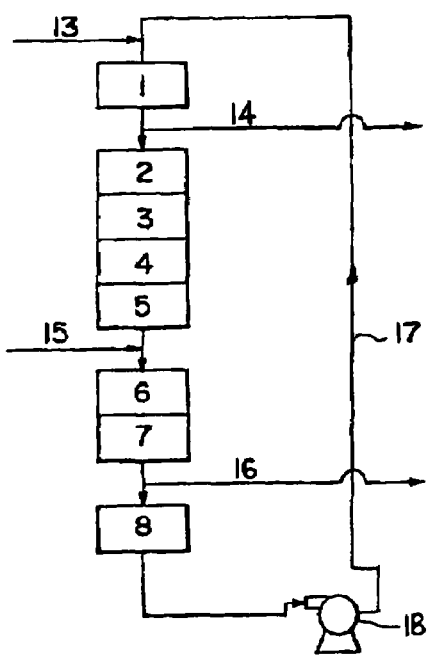
FIG. 2 is a schematic view showing another example of a simulated moving bed apparatus to be used in the present invention.

A method in the present invention will be described with reference to the drawings. FIG. 1 is a schematic view showing an example of a simulated moving bed apparatus to be used in the present invention, and FIG. 2 is a schematic view showing another example of a simulated moving bed apparatus to be used in the present invention.

In FIG. 1, the conduit is formed by connecting 12 columns in series. In FIG. 2, the conduit is formed by connecting 8 columns in series.

Although not shown, in each apparatus, all conduits for connecting the columns are connected with a conduit for supplying an eluent, a conduit for supplying a mixed solution, and conduits for discharging a liquid. The supply of the liquid and the discharge of the liquid from those conduits are controlled by an automatic valve. The number and sizes of the columns are determined by factors such as the kind and composition of the mixed solution, a flow rate, a pressure drop, and the size of the apparatus, and are not limited.

In the simulated moving bed chromatography using the above apparatus, the following adsorption operation, concentration operation, desorption operation, and eluent recovery operation as basic operations are continuously performed in a cyclic manner.

(1) Adsorption Operation

The mixed component in the mixed solution is brought into contact with the packing material, and is repeatedly adsorbed to and desorbed from the packing material owing to the flow of the supplied eluent. The degree to which the packing material adsorbs the extract component is larger than the degree to which the packing material adsorbs the raffinate component, so the rate at which the extract component moves in the column is small. The degree to which the packing material adsorbs the raffinate component is smaller than the degree to which the packing material adsorbs the extract component, so the rate at which the raffinate component moves in the column is large. As a result, the concentration distribution of the raffinate component precedes the concentration distribution of the extract component in the conduit.

(2) Concentration Operation

When the eluent containing the extract component is supplied to a packed bet to which the extract component is mainly adsorbed, the raffinate component remaining on the packing material is expelled, and hence the extract component is concentrated.

(3) Desorption Operation

When a larger amount of the eluent than that at the time of concentration of the extract component is supplied to the packed bed, the extract component that has been adsorbed to the packing material is desorbed from the packing material, and the rate at which the extract component moves in the column increases to be higher than that at the time of the concentration operation.

(4) Eluent Recovery Operation

When the amount of the eluent to be supplied to the packing material adsorbing the raffinate component is smaller than that at the time of adsorption of the raffinate component, the movement of the raffinate component moving in the conduit is suppressed. The packing material on a downstream side with respect to the point at which the amount of the eluent to be supplied reduces adsorbs a component in the eluent, and the eluent not containing such component is supplied to the conduit on the downstream side with respect to the point.

In FIG. 1, reference numerals 1 to 12 denote rooms in which packing materials are packed (adsorption chambers, columns) which are mutually connected in series. Reference numeral 13 denotes an eluent supply line; 14, an extract discharge line; 15, an optical isomer-containing solution supply line; 16, a raffinate discharge line; 17, a recycle line; and 18, a pump.

In the state of arrangement of the adsorption chambers 1 to 12 and the lines 13 to 16 as shown in FIG. 1, the desorption operation is conducted in the adsorption chambers 1 to 3, the concentration operation is conducted in the adsorption chambers 4 to 6, the adsorption operation is conducted in the adsorption chambers 7 to 9, and the eluent recovery operation is conducted in the adsorption chambers 10 to 12.

In such simulated moving bed, the respective supply lines and the respective discharge lines are shifted into one adsorption chamber one by one in the direction in which the liquid flows in the conduit at a constant time interval by operation of valves.

As a result, in the next state of arrangement of the adsorption chambers, the desorption operation is conducted in the adsorption chambers 2 to 4, the concentration operation is conducted in the adsorption chambers 5 to 7, the adsorption operation is conducted in the adsorption chambers 8 to 10, and the eluent recovery operation is conducted in the adsorption chambers 11 to 1.

Thus, by repeating this operation one after another, separation treatment of an optical isomer mixture is efficiently achieved.

In FIG. 1, an extract solution discharged from the extract discharge line 14 is supplied to a first falling film evaporator 19, a second falling film evaporator 20, and a wiped film evaporator 21 one after another, and is concentrated by these evaporators. The solvent vapor from the evaporators is sent to a recovery tank 22, and its composition is adjusted in an evaporation device 25, whereby the vapor is recycled as an eluent. The concentrate concentrated by the evaporators is sent to a reservoir 23, and a target optically active substance is obtained from the concentrate through operation such as recrystallization or distillation.

A raffinate solution collected from the raffinate discharge line 16 is mixed with the mixed solution via a racemization tank 24, and is subjected to separation by means of the chromatography again.

The simulated moving bed apparatus shown in FIG. 1 intends to produce an extract component, but can be constituted to intend to produce a raffinate component by replacing, for example, devices from the first falling film evaporator 19 to the evaporation device 25 with the racemization tank 24.

In addition, the simulated moving bed apparatus shown in FIG. 1 can be constituted to intend to produce both an extract component and a raffinate component by providing both the extract discharge line 14 and the raffinate discharge line 16 with, for example, devices from the first falling film evaporator 19 to the evaporation device 25.

In the state of arrangement of the adsorption chambers 1 to 8 and the lines 13 to 16 as shown in FIG. 2, the eluent recovery operation is conducted in the adsorption chamber 1, the adsorption operation is conducted in the adsorption chambers 2 to 5, the concentration operation is conducted in the adsorption chambers 6 and 7, and the desorption operation is conducted in the adsorption chamber 8. In such simulated moving bed, the respective supply lines and the respective discharge lines are shifted into one adsorption chamber one by one in the direction in which the liquid flows in the conduit at a constant time interval by operation of valves.

As a result, in the next state of arrangement of the adsorption chambers, the desorption operation is conducted in the adsorption chamber 2, the concentration operation is conducted in the adsorption chambers 3 to 6, the adsorption operation is conducted in the adsorption chambers 7 and 8, and the eluent recovery operation is conducted in the adsorption chamber 1. Thus, by repeating this operation one after another, separation treatment of an optical isomer mixture is efficiently achieved.

According to the simulated moving bed chromatography, Ethyl (3R,5S,6E)-7-[2-cyclopropyl-4-(4-fluorophenyl)quinoline-3-yl]-3,5-dihydroxy-6-heptenoate can be obtained as a raffinate component or an extract component. At the same time, the other component in the mixed solution can be obtained as the extract component or the raffinate component.

EXAMPLES

Hereinafter, the present invention will be described in detail based on examples. However, the present invention is not limited to the examples.

Although the following examples each show an example of separation by means of simulated moving bed chromatography, the present invention is not limited to separation under the conditions. Conditions such as a cycle time may be arbitrarily set for optimizing operation as disclosed in, for example, WO 00/26886.

Synthesis Example 1

Production of Column for HPLC Comprising Packing Material Carrying Cellulose tris(4-isopropylphenylcarbamate)

(1) Surface Treatment of Silica Gel

Porous silica gel (having a particle size of 20 μm) was allowed to react with 3-aminopropyltriethoxysilane by means of a conventionally known method to subject the porous silica gel to aminopropylsilane treatment (APS treatment).

(2) Synthesis of Cellulose Tris(4-isopropylphenylcarbamate)

Under a nitrogen atmosphere, 100 g of cellulose and 794.0 g of 4-isopropylphenylisocyanate (2.7 equivalents with respect to the hydroxyl groups of cellulose) were stirred in 3.2 L of dry pyridine at a pyridine reflux temperature for 60 hours. After that, 40 L of methanol were poured into the resultant. The precipitated solid was filtered through a glass filter, and was washed with methanol several times, followed by vacuum drying (80° C., 15 hours). As a result, 336.5 g of a slightly yellowish white solid were obtained (84.6% yield). Analyses of the carbon, hydrogen, and nitrogen elements of the resultant white solid are shown below.

| | CHN results: |
|---|---|
| Measured value | C %: 65.67 H %: 6.62 N %: 6.31 |
| Theoretical value | C %: 66.96 H %: 6.71 N %: 6.51 |

(3) Production of Silica Gel Carrying Packing Material of Cellulose Tris(4-isopropylphenylcarbamate)

100 g of cellulose tris(4-isopropylphenylcarbamate) obtained in the above item (2) were dissolved into 600 mL of acetone, and the obtained polymer dope was uniformly applied to 400 g of silica gel in the item (1). After the application, acetone was distilled off under reduced pressure to produce a target packing material carrying cellulose tris(4-isopropylphenylcarbamate).

(4) Production of Column for HPLC in Which Produced Packing Material is Packed

The packing material carrying cellulose tris(4-isopropylphenylcarbamate) produced in the above item (3) was packed in a stainless column having a length of 25 cm and an inner diameter of 0.46 cm by means of a slurry packing method to produce a column for HPLC.

Example 1

(1) Measurement of Retention Coefficient by Means of Column for HPLC Produced in Synthesis Example 1

Figure 3:
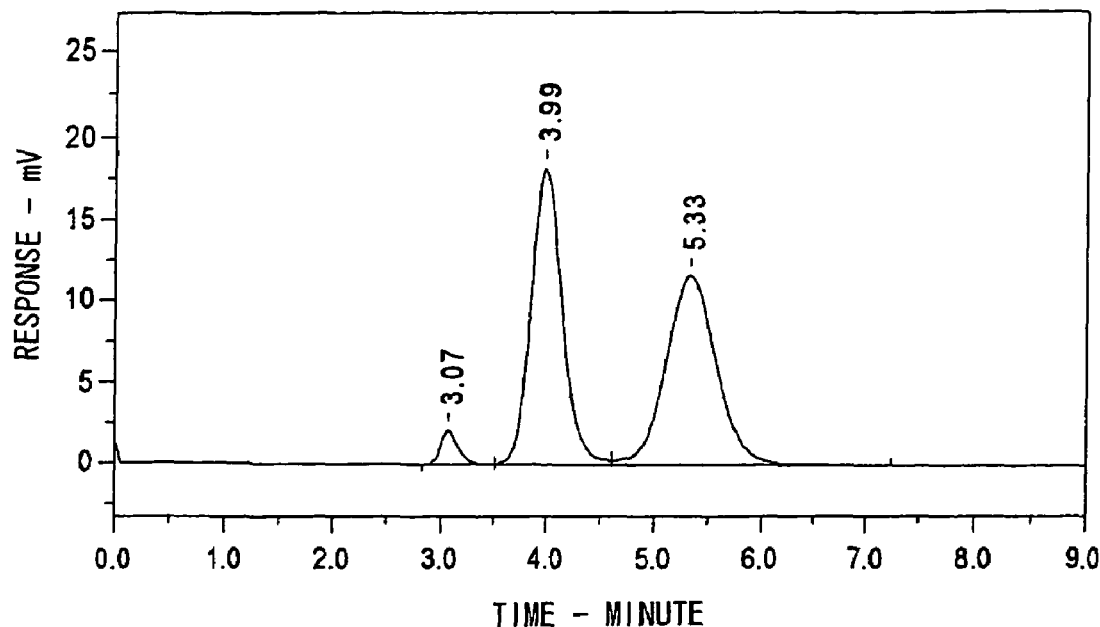
FIG. 3 is a chromatogram obtained in Example 1.

A liquid chromatography apparatus manufactured by JASCO (pump: PU-980, UV detector: UV-975, auto sampler: AS-950, column oven: 869-CO, system controller: LCSS-900) was used to analyze a mixed solution of Ethyl (3R,5S,6E)-7-[2-cyclopropyl-4-(4-fluorophenyl)quinoline-3-yl]-3,5-dihydroxy-6-heptenoate and Ethyl (3S,5R,6E)-7-[2-cyclopropyl-4-(4-fluorophenyl)quinoline-3-yl]-3,5-dihydroxy-6-heptenoate with the column for HPLC produced in Synthesis Example 1. Table 1 shows analysis conditions and the retention coefficient ($k_1'$) obtained as a result of the analysis. FIG. 3 shows a chromatogram obtained as a result of the analysis.

(2) Separation of Optical Isomer by Means of Simulated Moving Bed Chromatography The packing material produced in Synthesis Example 1 was packed in each of eight stainless columns each having an inner diameter of 1.0 cm and a length of 10 cm by means of a slurry packing method. Those columns were attached to a small simulated moving bed chromatograph preparative apparatus to fractionate an optical isomer from the mixed solution. Operating conditions in this example are shown below. Table 2 shows the optical purity of a ante-component (raffinate) and the optical purity of a post-component (extract) obtained as a result of operation of the small simulated moving bed chromatograph preparative apparatus, and ante-component productivity.

Operating Conditions
Mobile phase: n-hexane/2-propanol 50/50 (v/v)
Column temperature: 40° C.
Feed flow rate: 2.05 ml/min
Flow rate of raffinate: 2.58 ml/min
Flow rate of extract: 11.52 ml/min
Flow rate of eluent: 12.05 ml/min
Step time: 1.35 min
Feed concentration: 28 (mg/ml-mobile phase)

In the above operating conditions, the term "feed flow rate" refers to the rate at which the mixed solution is supplied, the term "flow rate of raffinate" refers to the rate at which the liquid is discharged in the second discharging step, the term "flow rate of extract" refers to the rate at which the liquid is discharged in the first discharging step, the term "flow rate of eluent" refers to the rate at which the eluent is supplied, the term "step time" refers to the time interval at which the supplying positions of the eluent and the mixed solution, and the first and second discharge positions are moved, and the term "feed concentration" refers to the concentration of a solute in the mixed solution. The solvent of the mixed solution has the same composition as that of the mobile phase (eluent).

The optical purity of each of the ante-component and the post-component was measured through analysis by means of a column for separating an optical isomer, CHIRALCEL OF (having an inner diameter of 0.46 cm and a length of 25 cm) manufactured by Daicel Chemical Industries, Ltd. Analysis conditions are shown below.
Mobile phase: hexane/2-propanol=8/2 (v/v)
Flow rate: 1.0 ml/min
Temperature: 25° C.
Detected wavelength: 254 nm
Injection amount: 1.0 mg/ml (hexane/2-propanol=1/1)×10 μl Comparative Example 1

Figure 4:
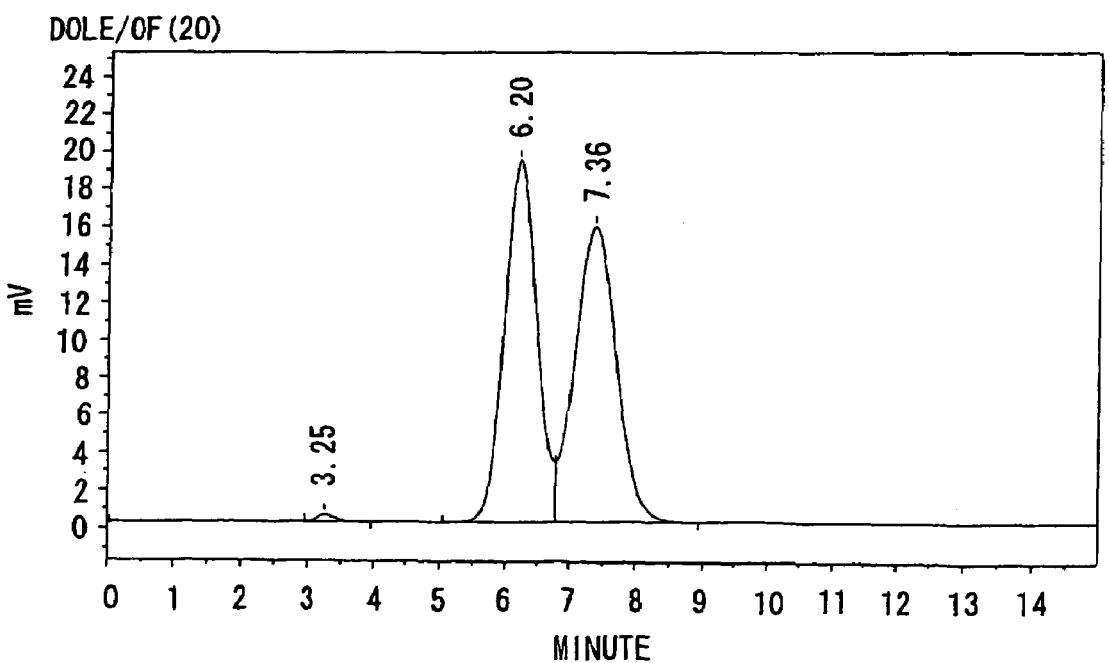
FIG. 4 is a chromatogram obtained in Comparative Example 1.

(1) Measurement of Retention Coefficient by Means of Column for HPLC in which Cellulose Tris(4-chlorophenylcarbamate) is Packed The mixed solution was analyzed in the same manner as in Example 1 except that: a CHIRALCEL OF (having a particle size of 20 μm) manufactured by Daicel Chemical Industries, Ltd., a column for optical resolution mainly comprising cellulose tris(4-chlorophenylcarbamate), was used; and the analysis conditions were changed to those shown in Table 1. Table 1 shows the analysis conditions and the retention coefficient ($k_1'$) obtained as a result of the analysis. FIG. 4 shows a chromatogram obtained as a result of the analysis.

(2) Separation of Optical Isomer by Means of Simulated Moving Bed Chromatography A small simulated moving bed chromatograph preparative apparatus was used to fractionate an optical isomer from the mixed solution in the same manner as in Example 1 except that: the packing material produced in Synthesis Example 2 was used; and the apparatus was operated under the following operating conditions. Operating conditions in this example are shown below. Table 2 shows the optical purity of a ante-component and the optical purity of a post-component obtained as a result of operation of the small simulated moving bed chromatograph preparative apparatus, and ante-component productivity.

Operating Conditions
Mobile phase: n-hexane/2-propanol 68/32 (v/v)
Column temperature: 40° C.
Feed flow rate: 1.05 ml/min
Flow rate of raffinate: 2.59 ml/min
Flow rate of extract: 9.32 ml/min
Flow rate of eluent: 10.86 ml/min
Step time: 1.5 min
Feed concentration: 20 (mg/ml-mobile phase)

TABLE 1

|  | Column used | Analysis conditions | Retention coefficient*[1] ($k_1'$) | Separation factor*[2] ($\alpha$) |
| --- | --- | --- | --- | --- |
| Example 1 | Product produced in Synthesis Example 1 | (1) | 0.300 | 2.46 |
| Comparative Example 1 | Product produced in Synthesis Example 2 | (2) | 0.908 | 1.39 |

<Analysis conditions>
(1) Mobile phase: n-hexane/2-propanol 50/50 (v/v), Flow rate: 1.0 mL/min, Temperature: 40° C., Detected wavelength: 254 nm, Injection amount: 1.5 mg/mL (mobile phase) × 2.5 μL
(2) Mobile phase: n-hexane/2-propanol 68/32 (v/v), Flow rate: 1.0 ml/min, Temperature: 40° C., Detected wavelength: 254 nm, Injection amount: 1.5 mg/mL (mobile phase) × 2.5 μL
*[1] $k_1'$ was determined from the following expression. $k_1' = (V_1 - V_0)/V_0$ (In the expression, $V_0$ represents the retention volume of tri-tert-butylbenzene and $V_1$ represents the retention volume of a raffinate component.)
*[2] $\alpha$ was determined from the following expression. $\alpha = k_2'/k_1'$ (In the expression, $k_2'$ represents the retention coefficient of an extract component which is determined from the following expression.) $k_2' = (V_2 - V_0)/V_0$ ($V_0$ represents the retention volume of tri-tert-butylbenzene and $V_2$ represents the retention volume of the extract component.)

TABLE 2

|  | Example 1 | Comparative Example 1 |
| --- | --- | --- |
| Mobile phase | (1) | (2) |
| Optical purity of raffinate (ante-component) (% ee) | 99.5 | 99.5 |
| Optical purity of extract (post-component) (% ee) | 95.0 | 94.6 |
| Productivity* (kg-Rac./kg-CSP/day) | 1.56 | 0.80 |

<Mobile phases>
(1) n-hexane/2-propanol = 50/50 (v/v)
(2) n-hexane/2-propanol = 68/32 (v/v)
*The weight (kg) of a racemic body that can be treated at one day/1 kg of the packing material.

INDUSTRIAL APPLICABILITY

According to the present invention, a packing material having excellent ability of optical resolution is used as a packing material for optical resolution to enable: the continuous optical resolution of an optical isomer with high productivity; and the continuous production of Ethyl (3R,5S,6E)-7-[2-cyclopropyl-4-(4-fluorophenyl)quinoline-3-yl]-3,5-dihydroxy-6-heptenoate with high productivity. Therefore, the present invention can be expected to significantly reduce a cost in industrial production of Ethyl (3R,5S,6E)-7-[2-cyclopropyl-4-(4-fluorophenyl)quinoline-3-yl]-3,5-dihydroxy-6-heptenoate.

The invention claimed is:

1. A method of obtaining Ethyl(3R,5S,6E)-7-[2-cyclopropyl-4-(4-fluorophenyl)quinoline-3-yl]-3,5-dihydroxy-6-heptenoate comprising separating Ethyl(3R,5S,6E)-7-[2-cyclopropyl-4-(4-fluorophenyl)quinoline-3-yl]-3,5-dihydroxy-6-heptenoate from a solution which comprises a mixture of optical isomers of Ethyl 6E-7-[2-cyclopropyl-4-(4-fluorophenyl)quinoline-3-yl]-3,5-dihydroxy-6-heptenoate by means of liquid chromatography using a packing material comprising a carrier and a polysaccharide derivative carried on the carrier, wherein the polysaccharide derivative, wherein at least a part of hydrogen atoms of hydroxyl and amino groups of the polysaccharide are substituted by one or two or more kinds of substituents each represented by the following general formula (1) or (2),

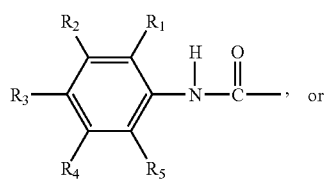 (1)

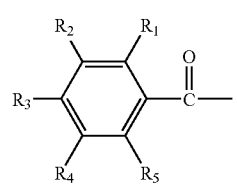 (2)

wherein in both formulae (1) and (2), at least one of $R_1$ to $R_5$ represents a linear or branched alkyl group having 3 to 8 carbon atoms, and the others each represent a substituent selected from hydrogen, halogen, or an alkyl group.

2. The method according to claim 1, wherein:
the polysaccharide derivative, wherein at least a part of hydrogen atoms of hydroxyl and amino groups of the polysaccharide are substituted by substituents represented by the general formula (1);
$R_3$ shown in the general formula (1) represents an isopropyl group; and
$R_1$, $R_2$, $R_4$, and $R_5$ shown in the general formula (1) each represent a hydrogen atom.

3. The method according to claim 1 or 2, wherein the liquid chromatography is continuous liquid chromatography with which at least one kind of component is continuously separated and collected from a mixed solution comprising two or more kinds of components.

4. The method according to claim 3, wherein the continuous liquid chromatography is simulated moving bed chromatography.

5. The method according to claim 1, wherein the polysaccharide derivative contains both of formula (1) and (2).

6. The method according to claim 1, wherein the polysaccharide derivative contains formula (1).

7. The method according to claim 1, wherein the polysaccharide derivative contains formula (2).

8. The method according to claim 1, wherein said polysaccharide derivative has a degree of polymerization of 5 to 1,000.

9. The method according to claim 1, wherein said polysaccharide derivative has a degree of polymerization of 10 to 500.

* * * * *